United States Patent [19]
Kingston

[11] Patent Number: 5,414,259
[45] Date of Patent: May 9, 1995

[54] METHOD OF SPECIATED ISOTOPE DILUTION MASS SPECTROMETRY

[75] Inventor: Howard M. Kingston, Evans City, Pa.

[73] Assignee: Duquesne University of the Holy Ghost, Pittsburgh, Pa.

[21] Appl. No.: 177,783

[22] Filed: Jan. 5, 1994

[51] Int. Cl.⁶ .................... B01D 59/44; H01J 49/00
[52] U.S. Cl. ................................ 250/283; 250/282
[58] Field of Search ............... 250/282, 283, 284, 288

[56] References Cited

U.S. PATENT DOCUMENTS

| | | | |
|---|---|---|---|
| 3,786,249 | 1/1974 | Anbar et al. | 250/283 |
| 4,022,876 | 5/1977 | Anbar | 250/282 |
| 5,352,893 | 10/1994 | Freedman | 250/282 |

*Primary Examiner*—Bruce C. Anderson
*Attorney, Agent, or Firm*—Arnold B. Silverman

[57] ABSTRACT

The method of determining the concentration of a specie in a sample includes providing at least one predetermined, enriched isotope in the same speciated form as the species to be measured, spiking the sample containing the species to be measured, equilibrating the spiked species with the species to be measured, separating the species from the sample and subsequently determining the concentration of the species to be measured by employing isotopic element specie ratios. In one embodiment, a single speciated isotope spike is employed and, in others, two or more such spikes may be employed. In a preferred embodiment, time resolution chromatography is used to effect separation of these species from the sample and mass spectrometer is employed in determining isotopic elemental ratios. It is also preferred that a method be employed to determine if there has been conversion from one species to another. In another embodiment, spiking of the several different isotopically enriched analogs of the same specie are added at various steps in the sampling procedure and the stability and integrity of the specie with respect to these processes is evaluated by mass spectrometric measurements of the various isotopic ratios. Chemical processes, extraction methods, dissolution procedures and storage procedures are evaluated. In another embodiment, speciated isotope dilution is used to determine the effect on species of various sample preparation methods and portions of sample preparation techniques. Extraction and separation procedures employ the technique to provide definitive evidence of accurate specie manipulation and provide for performance based measurement.

19 Claims, 1 Drawing Sheet

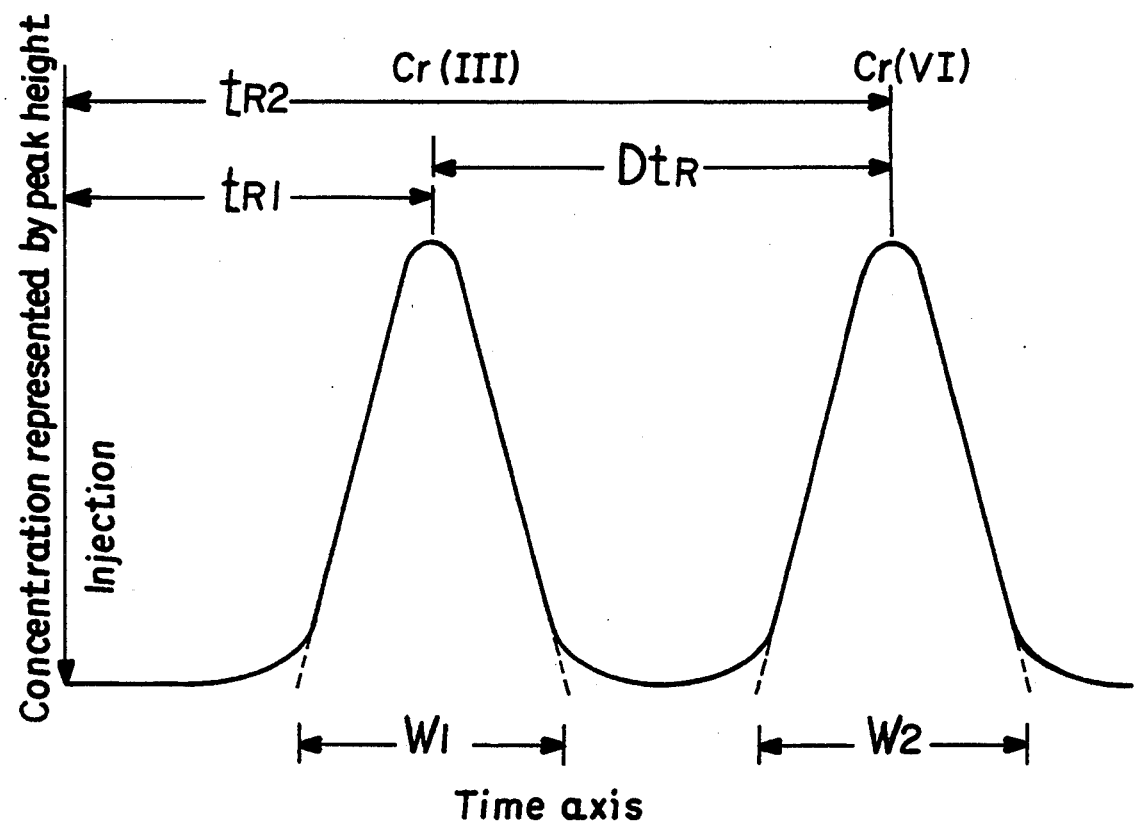

METHOD OF SPECIATED ISOTOPE DILUTION MASS SPECTROMETRY

BACKGROUND OF THE INVENTION

1. Field Of the Invention

The present invention relates to a method of measurement of species which employs enriched isotope spikes in the same speciated form as the species to be measured, equilibration, separation and subsequent determining of concentration by employing isotopic element specie ratios.

2. Description Of the Prior Art

The need for making quantitative determinations of a specie of interest occurs in many environments including environmental, biological, pharmaceutical and industrial samples. For example, certain forms of an element or molecular species may exhibit different toxicities or chemical behaviors from others. Existing techniques, with the exception of electrochemical methods, rely predominately on physical separation in time. They are incapable of determining either cross-over (transformation of one specie form into another), are lost, are altered or are completely recovered. Such techniques cannot be used to determine transformation of one species into another during storage, manipulation and sample preparation or during the measurement process.

An example of the criticality of such measurements would be to consider chromium. While Cr(III) is a trace dement essential for human health, Cr(VI) is poisonous to humans and most other animals and is also a carcinogen. As a result, the difference between these two species, which resides in the oxidation state of the dement, may be of critical importance. While chromatography can be used to separate Cr(III) in time resolution from Cr(VI), as each specie can react with its surroundings and even with separating agencies, the chromatographic separation is only a snapshot in time recording the state of affairs at the end of the manipulation. Each specie may have reacted with many other reagents and transformed during the analysis. There is, therefore, with time resolution, no way of determining how much chromium was actually in each specie when the experiment began or when the sample was actually taken.

Specific species are often required for a particular process. For example, barium is toxic in some compound forms, but is prescribed for medical diagnostic x-ray tests, usually as barium sulfate in liquid slurry form. The conformation and evaluation of a body's processing of barium into another specie can be accomplished with isotopically labeled barium sulfate. These studies have been done, but the use of speciated isotope dilution measurements has not been used for analysis.

Some isotopic tracking has been done for lead due to terrestrially unique and naturally occurring isotopic compositions of this dement. The isotopic ratios can be matched with a particular source to determine the origin of the lead. These measurements are not speciated measurements, but depend on the isotopic ratio differences of the natural material to be detected. This technique has also been used for lead pottery glazes to determine the origin of art objects, however in this case also, naturally occurring isotopic ratios were determined. Lead is a uniquely feasible non-radioactive dement to be evaluated (as to origin) by the isotopic ratio method, as its isotopic ratios change with the amount of uranium mixed with the lead in the original ore deposits. The decay of uranium into different lead isotopes creates unique isotopic ratios for different lead deposits. Uranium also permits this origin-specific ratio identification method.

All elements, with the exception of Pb, U, and Pu, have constant isotopic ratios throughout the earth's crust. Hinners, T. A.; Heithmar, E. M.; Spittier, T. M.; Henshaw, J. M., "Inductively Coupled Plasma Mass Spectrometric Determination of Lead Isotopes" Analytical Chemistry, 59, 2658-2662, 1987. It is this constant elemental isotopic ratio that provides the basis of isotope dilution analysis. When this ratio for an element is artificially altered with an enriched isotope of that element, and bulk analysis of an element is measured from the isotopic ratio, the method is referred to as isotope dilution analysis. The measurement employs a mass spectrometer to determine the isotopic ratio, but only the total elemental concentration is determined. Examples of isotope dilution analysis for total elemental concentration are described for standard reference materials and for general analysis using thermal isotope dilution mass spectrometry. See Moore, Larry J.; Kingston, Howard M.; Murphy, Thomas J.; and Paulsen, Paul J., "The Use of Isotope Dilution Mass Spectrometry for the Certification of Standard Reference Materials", Environment International, 10, 169-173, 1984; Fassett, Jack D. and Paulsen, Paul J., "Isotope Dilution Mass Spectrometry for Accurate Elemental Analysis", Analytical Chemistry, 61, 386-390, 1989. Specific analysis of total chromium and selenium and other metals by this method of isotope dilution mass spectrometry using a gas chromatography mass spectrometer (GC-MS) are described in other references. Reamer, Donald C. and Veillon, Claude, "A Double Isotope Dilution Method for Using Stable Selenium Isotopes in Metabolic Tracer Studies: Analysis by Gas Chromatography/Mass Spectrometry (GC/MS)", Journal of Nutrition, 113, 786-792, 1983. Reamer, Donald C. and Veillon, Claude, "Determination of Selenium in Biological Materials by Stable Isotope Dilution Gas Chromatography-Mass Spectrometry", Analytical Chemistry, 53, 2166-2169, 1981. Veillon, Claude; Wolf, Wayne, and Guthrie, Barbara, "Determination of Chromium in Biological Materials by Stable Isotope Dilution", Analytical Chemistry, 51, 1022-1024, 1979.

Examples of typical prior art are those that use ICP-MS detection with some form of chromatography (sometimes called "flow injection analysis") to separate the species and then uses the instrument as a total elemental detector as described in Thompson, J. J.; Houk, R. S., "Inductively Coupled Plasma Mass Spectrometric Detection for Multielement Flow Injection Analysis and Elemental Speciation by Reversed-Phase Liquid Chromatography" Analytical Chemistry, 58, 2541-2548, 1986. As previously stated herein, in general, when isotope dilution has been used with inductively coupled plasma for environmental analysis, the applications have focused on total analysis and although it is an excellent method for total elemental composition, it has not been effectively applied to species. Examples of ICP-MS isotope dilution analysis for environmental natural water and geological samples are given in Garbarino, H. R.; Taylor, H. E., "Stable Isotope Dilution Analysis of Hydrologic Samples by Inductively Coupled Plasma Mass Spectrometry" Analytical Chemistry, 59, 1568-1575, 1987; McLaren, J. W.; Beauchemin, D.; Berman, S. S., "Application of Isotope Dilution Inductively Coupled Plasma Mass Spectrometry to the Analysis of Marine Sediments" Analytical Chemistry, 59, 610–613, 1987, respectively.

Studies to measure metabolic transformation of elements in humans have been performed where stable isotopes, such as Se-74, have been metabolized in the body and transformed into various species. An enriched isotope is ingested as an inorganic salt and the different forms of the isotope are made by the body. By feeding Se-74 to patients, allowing metabolism, and then removing and storing the blood, previously metabolized Se could be stored for each individual. After the body was free of the labeled Se-74, 11 months later, the blood was reintroduced into the subject and the exact excretion method was studied without the normal body burden of Se confusing the excretion in body fluids. This experiment used stable isotope tracers to studied blood excretion mechanisms and definitively established the dominant pathway to be the urinary path. The studies observed whether body pools could be labeled and how the element is excreted. The metabolic study was specifically for selenium and no specific speciated isotopes or specific species were used to spike in the measurement process. The species were destroyed in the measurement process and total selenium was reported. Following repeated ingestion of an enriched stable isotope of selenium, their blood plasma became labeled with the element in all of the natural, biologically relevant chemical forms. Veillon, Claude; Patterson, Kristine; Button, Lawrence; and Sytkowski, Arthur, "Selenium Utilization in Humans: a Long-Term, Self-Labeling Experiment with Stable Isotopes", American Journal of Clinical Nutrition 52, 155–158, 1990. By spreading the enriched isotope over all species the identification of any specific species becomes impossible by speciated isotope dilution mass spectrometry. "Selenium Utilization in Humans—A Long-Term, Self-Labeling experiment with stable Isotopes", Veillon et at., Am. J. Clin, Nutr.; 52:155–8 (1990) describes this study. Reamer, Donald C. and Veillon, Claude, "A Double Isotope Dilution Method for Using Stable Selenium Isotopes in Metabolic Tracer Studies: Analysis by Gas Chromatography/Mass Spectrometry (GC/MS)", Journal of Nutrition, 113, 786–792, 1983 describes the measurement method of isotope dilution using GC-MS. This method is identical to conventional isotope dilution mass spectrometry as described in Moore, Larry J.; Kingston, Howard M.; Murphy, Thomas J.; and Paulsen, Paul J., "The Use of Isotope Dilution Mass Spectrometry for the Certification of Standard Reference Materials", Environment International, 10, 169–173, 1984; and Fassett, Jack D. and Paulsen, Paul J., "Isotope Dilution Mass Spectrometry for Accurate Elemental Analysis", Analytical Chemistry, 61, 386–390, 1989, except for the type of mass spectrometry equipment used.

Since different species have different reactivates and can react with reagents, container material, oxygen from the air, or other portions of the sample itself, only a final indication of the species separated and detected in time has been employed. The original condition, or the ratio and type of species at the time of sampling or in the sample prior to sampling, cannot be assessed with certainty because transformations or exchanges of the species during storage, chemical manipulation, or the measurement process cannot be measured by conventional species measurement techniques.

Traditional speciation methods rely on separation of the species using physical and/or chemical separation methods. These methods have been summarized in two books. *Trace Element Speciation: Analytical Methods and Problems*, Ed. Graeme E. Batley, CRC Press, Boca Raton, Fla., 1989 (ISBN 0-8493-4712-2); and *Metal Speciation: Theory, Analysis and Application*, Eds. James R. Kramer and Herbert E. Allen, Lewis Publishers, Chelsea, Mich., 1991 (ISBN 0-87371-140-8). Neither reference mentions the word "isotope" and no mention of isotopic differentiation, isotopic spike equilibration, or measurement or monitoring using isotopes is mentioned in the speciation literature. Currently, chromatography and other methods of chemical and physical separation are used to perform speciation. Examples of these specific methods are compiled in the Batley and Kramer books, and additional examples are provided.

Aspects of elemental speciation for biological materials are reviewed in Behne, Dietrich, "Speciation of Trace Elements in Biological Materials: Trends and Problems", Analyst, 117, 555–557, 1992. The scope of speciation as related to high performance liquid chromatography can be understood from Cappon, C. J. "HPLC Speciation of Selected Trace Elements" LC-GC, 6, 584–599. 1988.

Early work in chromium speciation prior to spectroscopic equipment is described in Jones, D. R. and Manahan, S. E., "Atomic Absorption Detector for Chromium Organometallic Compounds Separated by High Speed Liquid Chromatography", Analytical Letters, 8, 569–574, 1975. Two current methods for determining chromium species in water, including one commercial version, are described in Lan, Chi-Ren; Tseng, Chia-Liang; Yang, Mo-Hsiung; and Alfassi, Zeer B., "Two-Step Coprecipitation Method for Differentiating Chromium Species in Water Followed by Determination of Chromium by Neutron Activation Analysis", Analyst, 116, 1991; and Determination of Chromium, Application Note 26, Dionex Corporation, May 1986. Energy based separation using microwave extraction is described in Ganzler, K.; Szinai, I.; and Salgo, A., "Effective Sample Preparation Method for Extracting Biologically Active Compounds From Different Matrices by a Microwave Technique", Journal of Chromatography, 520, 257–262, 1990. Most of these methods could be converted to a definitive speciation technique with the addition of spiking with a stable separated isotope specie and use of mass detection following the particular separation method described.

Currently, no definitive method of species measurement is available, although research is needed on many important species of almost every element. In addition to more than 100 elements, literally thousands of species of these elements need to be studied and evaluated. Organic molecules also need investigation. To evaluate the significance and reactions of each, a definitive measurement method is proposed that will work for all elements having more than one isotope. Elements that have radioactive isotopes can also be evaluated. For the examples previously given, chromium has four stable isotopes at constant ratio in nature (Cr-50 at 4.35%, Cr-52 at 83.79%, Cr-53 at 9.50%, and Cr-54 at 2.36%). Within the limits of current isotopic measurement, these ratios are constant throughout the entire earth's crust.

There remains, therefore, a very real and substantial need to provide a method for measuring quantitatively and accurately one or more species within a sample employing speciated isotope dilution measurement and sampling techniques.

SUMMARY OF THE INVENTION

The method of the present invention employs speciated isotope dilution in measuring or preparing a sample. It includes providing at least one speciated enriched isotope spike in the same speciated form as the species to be measured, spiking the sample containing the species to be measured therewith, and equilibrating said spiked species with said species to be measured, separation of the species to be measured and the enriched isotope spike from the remainder of the sample is then effected. Subsequently a determination of the concentration of the species to be measured is made by employing isotopic element specie ratio.

In preferred embodiments of the present invention, time related chromatographic means may be employed to effect the separation and a mass spectrometer may be employed in the isotope dilution measurements.

In a preferred process of the method, a determination as to whether isotopic conversion has occurred is made.

It is an object of the present invention to provide a method of measurement of elemental, ionic, molecular or complex species using isotope spiking of species, separation and isotope dilution fraction measurement to provide a determination of the quantity of the species in the example.

It is an object of the present invention to effect such determination by chemical means.

It is an object of the present invention to effect such determination by a combination of energy coupling and chemical means such as microwave or infrared energy.

It is a further object of the invention to employ such method in both measurement and sample preparation.

It is yet another object of the present invention to accomplish this objective by determining the oxidation state of the elemental species, ionic species, molecular species or complex species, such as organometallic species.

It is a further object of this invention to provide such determinations in an accurate, economical and reliable fashion.

Other objects of the invention will be more fully understood from the following description of the invention on reference to the illustration appended hereto.

BRIEF DESCRIPTION OF THE DRAWING

The FIGURE is an example of a time versus concentration plot employed in connection with examples disclosed herein.

DESCRIPTION OF THE PREFERRED EMBODIMENTS

As used herein, "specie" as employed in respect of the sample containing the specie which is to be analyzed quantitatively, shall refer to elemental species, ionic species, molecular species, complex species such as organometallic species and other species which are adapted to chemical quantitative speciated analysis of the present invention.

As used herein, the term "isotopic element specie ratio" shall refer to an isotopic ratio of a "specie."

The pure isotopic spikes (99.99+ % single separated isotopes) which may advantageously be employed in the present invention as the speciated isotope spike may be obtained from suitable sources known to those skilled in the art such as pure isotopic spikes which may be obtained from Los Alamos National Laboratories or enriched, separated isotopes spikes which are available from many sources including Los Alamos National Laboratories and Oak Ridge National Laboratories. These latter spikes are generally more than 90% enriched in the minor isotopes of interest.

In the method of the present invention (speciated isotope dilution), one or more spikes (speciated enriched isotope) will be prepared from an enriched isotope (usually a stable isotope), and the specie form of the spike will be altered to match that of the specie of interest of a particular element or molecule. More than one specie can be prepared from different enriched isotopes, depending on the number of available separated isotopes and depending on the number of isotopes the element of interest has. The spike will be added to the material that is to have the species determined. The specie's isotopic spike and the sample's natural specie will be equilibrated and extracted and/or separated physically by some means. This can be done in either a batch or on-line continuing mode. The isotopic specie spike and natural specie from the sample are both separated from the sample as they now have the same chemical reactivity and are chemically indistinguishable, with the exception of mass. Both are separated from other species in time and space and both have the same reactivity as that particular specie. As in the measurement method of isotope dilution mass spectrometry (IDMS), the measurement is made on the isotopic spike ratio. This leads to the evaluation of different isotopic ratios to determine the concentration of the species. In IDMS, the total concentration is calculated from the isotopic ratio. In this case, only the specie of interest will be present and only the specie concentration will be calculated. Two or more species can be measured simultaneously by using multiple spikes. The absence of a separated isotopic spike of one form in the other definitively demonstrates the absence of conversion of one specie to another. Any conversion of the specie of interest to another form will alter the isotopic ratio of that other specie form by the amount of spike and natural specie that was transformed in the measurement process.

The method of the present invention relies on several procedures that are summarized as follows:

The sample is defined and selected by the analyst and may be one of a variety of sample types previously described herein.

1. Tag the specie(s) in the sample with an isotopic tag in the same speciated form as the specie(s) of interest in the sample;
2. Equilibrate the spiked specie(s) with the natural sample specie(s) to thereby facilitate all chemical reactions occurring in equal probability to both the tagged specie and the natural specie.
3. Separate the specie(s) of interest from one another by some method, either chemical or physical, including but not limited to chromatography, digestion, extraction, centrifugation;
4. Determine each isotopic dement specie ratio, such as by using a mass spectrometer, for example. The total concentration of the fraction containing the specie(s) is also determined by standard methods for comparison;
5. Deconvolute the movement between species from the time of spiking, using isotopic ratios and other mathematical methods. The shifting of the ratio of any other specie from natural provides the cross over to that specie from the specie of interest under study. The absence of any ratio alteration from the speciated isotope, except for the specie of interest, definitively proves no crossover occurred;

6. Calculate the concentration of the specie(s) in the sample. While both conventional and the speciated isotope dilution can be employed simultaneously, only the speciated method can definitively prove whether all the specie of interest is in the original form as spiked;

7. Spiking can be just prior to measurement or at the time of sampling to determine the original concentration and stability of the species in the entire measurement process. The speciated isotope dilution method can be used to determine only measurement parameters, or can include sampling stability and chemical manipulation procedures, depending on the time and conditions of spiking. Lack of isotopic alteration of other species is definitive evidence of a lack of interchange between species.

These steps remain essentially the same if more than one specie is spiked, but the mathematical deconvolution is different, depending on the number of spiked species and the extent to which the species interact.

The calculations can be done by many different methods. The classical IDMS equations which are known to those skilled in the art may be employed where there is no crossover and may be employed with modification where crossover has occurred.

In the method disclosed herein, the traditional IDMS equation methods of calculating the concentration of an isotopically spiked portion of a sample are used in a different manner. The normal equilibration with spike and destruction of different species limit the information to bulk total elemental analysis. In this approach, the speciated information is retained and treated in an entirely different manner, preserving the species and separating them in time and space to permit quantitative and qualitative specie determinations. The traditional application of IDMS was developed as a measurement technique for the nuclear industry and was later applied to the geological community where isotopic composition is the main objective and speciation is ignored. The traditional use of the bulk element (total element), high accuracy analysis technique of IDMS is described in Moore, Larry J.; Kingston, Howard M.; Murphy, Thomas J.; and Paulsen, Paul J., "The Use of Isotope Dilution Mass Spectrometry for the Certification of Standard Reference Materials", Environment International, 10, 169–173, 1984; Fassett, Jack D. and Paulsen, Paul J., "Isotope Dilution Mass Spectrometry for Accurate Elemental Analysis", Analytical Chemistry, 61, 386–390, 1989; and Kingston, H. M. and Fassett, J. D., "Report of Analysis: Determination of Vanadium in Oil"; National Bureau of Standards, Gaithersburg, Md., Jul. 17, 1984.

Speciated measurements are based on transforming the enriched speciated isotope ("spike") into the same speciated form as the specie of interest. This is then added to a sample. The sample is then equilibrated. Equilibration is achieved by various methods depending on the medium in which the specie is found. For aqueous or other solutions, mixing prior to any manipulation is all that is necessary. Mixing the spike with the sample can occur at sampling or at the time of analysis. The ramification of one is the inclusion of storage, and the other is only from the analysis point. Solids such as tissues or soils prior to decomposition or extraction and the spike and specie are extracted or the material around them is decomposed at the same time to provide a homogeneous solution which is mixed at the molecular level and any chemical process happening to the one happens to the other with equal probability as they are indistinguishable chemically.

After equilibrating, the altered speciated spike isotope with the natural element species in the sample, physical separation of the individual species is performed. Isotopic element specie ratio analysis, preferably by mass spectrometry, is performed on each separate component (specie) and is used to measure the altered isotopic element specie ratio(s). The measured isotope ratio of isotope A to isotope B (Rm) can be calculated as follows:

$$Rm = \frac{A_x C_x W_x + A_s C_s W_s}{B_x C_x W_x + B_s C_s W_s}$$

Where:
$R_m$ is the measured isotope ratio of isotope A to isotope B
$A_x$ is atom fraction of isotope A in the sample (usually a constant ratio in nature)
$C_x$ is concentration of speciated element in the sample
$W_x$ is the weight of sample
$A_s$ is atom fraction of speciated isotope A in the spike (an enriched separated isotope)
$C_s$ is concentration of speciated elemental in the spike
$W_s$ is the weight of the isotopic spike
$B_x$ is atom fraction of isotope B in the sample (usually a constant ratio in nature)
$B_s$ is atom fraction of speciated isotope B in the spike (an enriched separated isotope)

See generally Fassett et al., "Isotope Dilution Mass Spectrometry for Accurate Elemental Analysis," Analytical Chemistry, Vol. 61, No. 10 (1989).

With a speciated spike, preservation and separation of the species, and analysis of individual isotopically spiked species, the concentration of the speciated element in the sample is calculated as distinguished from the total elemental concentration. The concentration of the specie without crossover is calculated as follows:

$$Cx = \frac{C_s W_s}{W_x} \cdot \frac{A_s - R_m B_s}{R_m B_x - A_x}$$

The method can best be demonstrated through examples. The combination of isotope transformation into a speciated form, species, equilibration, spike and natural species separation, and determination of isotopic element specie ratios for individualized species can be illustrated for chromium (III) and chromium (VI) with reference to the figure. The FIGURE illustrates the chromatographic separation of Cr(VI) and Cr(III). The FIGURE includes the separated isotope ratio to be measured by using Cr-50 separated isotopes equilibrated in the separate speciated forms of Cr(VI)-50 in the sample spiked and equilibrated with the enriched separated isotope.

A general overview of the preferred process of the present invention may be summarized as follows. The method being disclosed is generally feasible for most elements with multiple isotopes, multiple species (either ionic, molecular, metallic or complexed), and a method of physically separating the species. The technique being described uses separation methods that separate the elemental species physically and, in time from one another to permit the isotopic dement specie ratios of each specie to be determined independently.

The general concept is applicable to single or double spikes of ionic, molecular, or combination species (including metallic species). The first example considered herein uses the two oxidative elemental species Cr(III) and Cr(VI). This example will determine the concentration of Cr(VI) and indicate if any of it was transformed into Cr(III) during sample storage, separation, or manipulation.

EXAMPLE I

This example is shown graphically in the FIGURE.

Step 1. Spike Preparation

A separated (enriched) isotope spike for a single or for each of two species is prepared for Cr(VI) employing the single enriched specie spike of Cr-50 for Cr(VI). The breakdown is as follows:

| Separated Isotopic Spike | Natural Isotopic Abundance for Chromium (VI) |
|---|---|
| 50- Cr(VI) Spike | 50- 4.35% |
| 50- >99.99% | 52- 83.79% |
| 52- <0.01% | 53- 9.50% |
| 53- <0.01% | 54- 2.36% |
| 54- <0.01% | 50- 4.35% |

Know to 3+ significant figures ±0.02%

Step 2. Sample Collection and Spiking

Water is collected from a natural water aquifer. Using the single enriched specie spike of Cr-50 for Cr(VI), the sample is spiked with a known quantity of the spiked (Cr-50, Cr(VI)) species.

The optimal ratio would be Cr(VI)-50 in a concentration that approaches approximately a 1:1 ratio with the natural Cr(IV)-52. This permits the highest accuracy during the measurement.

Step 3. Sample Specie and Spike Specie Equilibration

Equilibrate the sample (natural) Cr(VI) isotope 52 (83.79%) and the species Cr(VI) spike isotope Cr-50. For this example, mixing both the natural and enriched material in aqueous form is accomplished. At this point the total Cr(VI) has a concentration from total material and a ratio Cr(VI)-50 (concentration established) to: Cr(VI)-52 in the sample of approximately 1:1 depending on the amount spiked, the purity of the isotope and the amount of Cr(VI) in the original sample.

Step 4. Resolve the Species Temporally or Spatially

For this example, separate the species using chromatography. (The preferred method of separation will be determined by the chemistry of the species and will be known to those skilled in the art.) Separation in time on-line to an inductively coupled plasma mass spectrometer (ICP-MS) creates physical resolution of Cr(III) fraction and Cr(VI) fraction in different portions of a chromatogram. Cr(III) and Cr(VI) are separated from each other and all isotopes of chromium in each speciated form are separated as one of these Cr(III) or Cr(VI) speciated forms and are separated together in narrow chromatographic bands.

Step 5. The Isotope Ratio of Each Speciated and Resolved Component is Measured

Isotope ratio measurement of each individual species (isotope resolved component is made separately for Cr(III) and for Cr(VI).

The concentration of the species is determined from isotope dilution calculations. A total concentration for both isotopes can also be performed as a check.

Step 6. Determination Of Specie Conversion

Deconvolute each species in the presence of each other using isotopic element specie ratios. If, for example, Cr(VI) was converted to Cr(III), the natural ratio will show a shift in the Cr(III)-50 isotopic ratio. If no Cr(VI) was converted to Cr(III), then the isotopic ratio of Cr((III) will be that of natural Cr. A natural isotopic ratio for Cr(III) definitely proves no conversion of Cr(VI) to Cr(III). This definitively proves the maximum concentration of Cr(VI) in the water. The FIGURE illustrates this example.

If Cr(III) was converted to Cr(VI), the Cr(VI) concentration will be increased and show a larger concentration. This experiment will only provide a definitive maximum concentration for Cr(VI).

To definitively determine both Cr(III) and Cr(VI), Step 1 would be altered for a double speciated isotopic spike. This is described in connection with Example II.

With reference to the FIGURE, a specific example of the general concept to be applied with a single specie spike of ionic Cr(VI) is illustrated.

| Natural Isotopic Abundance for Cr Spike | Separated Isotopic Spike |
|---|---|
| 50- 4.35% | 50- Cr(VI) |
| 52- 83.79% | 50- >99.99% |
| 53- 9.50% | 52- <0.01% |
| 54- 2.36% | 53- <0.01% |
| 50- 4.35% | 54- <0.01% |

| | Cr(III) | Cr(VI) |
|---|---|---|
| B. Spike Resolution | | |
| Nat. Cr(III) & (VI) | Nat. Cr(III) | Nat. Cr(VI) |
| 52- 83.79% | 52- 83.79% | 52- 83.79% |
| 53- 9.50% | 53- 9.50% | 53- 9.50% |
| 54- 2.36% | 54- 2.36% | 54- 2.36% |
| 50- 4.35% | 50- 4.35% | 50- 4.35% |
| | | 50- Cr(VI) Spike |
| | | 50- >99.99% % |
| | | 52- <0.01% |
| | | 53- <0.01% |

The ratios are as follows:

$$\text{Crx(III)} \frac{52}{50} \frac{83.79}{4.35} \qquad \text{Crx(VI)} \frac{52}{50} \frac{83.79}{4.35}$$

$$\text{Crsp(VI)} \frac{52}{50} \frac{0.01}{99.99}$$

$$\text{Crxsp(III)} \frac{52}{50} \frac{83.79}{4.35} \qquad \text{Crxsp(VI)} \frac{52}{50} \sim \frac{1}{1}$$

Where "x" is the sample specie, "sp" is the spike specie, and "xsp" is the final combination of sample and spike for a single specie. This process provides the ratio measurement of 52:50 for Cr(VI) and for Cr(III) that establishes the stability or lack of stability of the species during storage, sample preparation, processing and analyzing. It also provides for quantification of Cr(VI) if no conversion occurred.

EXAMPLE II

This example provides a definitive determination of both Cr(III) and Cr(VI).

If Cr(III) was converted to Cr(VI), the Cr(VI) concentration will be increased and show a larger concentration. This experiment will only provide a definitive maximum concentration for Cr(VI).

To definitively determine both Cr(III) and Cr(VI), Step 1 of Example I would be altered for a double speciated isotopic spike.

Example II is shown graphically in the FIGURE. Only steps 1, 5 and 6 of Example I are altered in Example II.

Step 1. Spike Preparation

Separated (enriched) isotope spikes for both Cr(III) and Cr(VI) species are prepared. Use the isotopically enriched specie spike of Cr-50 for Cr(VI), as in Example I, and the isotopically enriched specie spike of Cr-53 for Cr(III):

| Natural Isotopic Abundance for Cr (III) & (VI) | Enr. Isotope Cr(VI)-50 Separated Isotopic Spike | Enr. Iso. Cr(III)-53 Sep. Isotopic Spike |
|---|---|---|
| 50- 4.35% | 50- Cr(VI) Spike | 53- Cr(III) Spike |
| 52- 83.79% | 50- >99.99% | 50- <0.01% |
| 53- 9.50% | 52- <0.01% | 52- <0.01% |
| 54- 2.36% | 53- <0.01% | 53- >99.99% |
| 50- 4.35% | 54- <0.01% | 54- <0.01% |

Know to 3+ significant figures ±0.02%

Steps 2 through 5 are essentially the same as in Example I.

Step 2. Sample Collection and Spiking
Step 3. Sample Specie and Spike Specie Equilibration
Step 4. Resolve the Species Temporally or Spatially
Step 5. Isotope Ratio of Each Speciated and Resolved Component
Step 6. Determination of Specie Conversion and Concentration Deconvolute each specie in the presence of the other using isotopic element specie ratios. If Cr(VI) was converted to Cr(III), the natural ratio will show a shift in the Cr(III)-50 isotopic ratio Cr52/50. If no Cr(VI) was converted to Cr(III), then the isotopic ratio of Cr(III) will be that of natural Cr52/50. If no Cr(III) was converted to Cr(VI), then the isotopic ratio of Cr(VI) will have a normal Cr52/53 ratio (to within 0.04%, or the ability of the instrument to determine the ratio). The absence of other than a natural isotopic ratio for Cr(iii) Cr52/50 precludes the conversion of Cr(VI) to Cr(III). The equation as described can be used to definitively calculate the concentration of Cr(III) [Cr(III) 52/53] species and Cr(VI) [Cr(VI) 52/50] species in the water.

One may determine the extent of conversion of each specie to another, and one or both may need to be corrected for conversion in different examples. The relative concentration and quantity of each isotope converted to the other can be calculated using mathematical relationships established for the specific isotopes, enrichment factors, and resolutions of the analyzing instrument.

With reference to Example I and the FIGURE, a specific example of the general concept to be applied with double spike of ionic chromium (III) and (VI) species will be considered. The data is as follows:

| A. Time Resolution | Cr(III) | Cr(VI) |
|---|---|---|
| B. Spike Resolution | | |
| Nat. Cr(III) & (VI) | Nat. Cr(III) | Nat. Cr(VI) |
| 50- 4.35% | 50- 4.35% | 50- 4.35% |
| 52- 83.79% | 52- 83.79% | 52- 83.79% |
| 53- 9.50% | 53- 9.50% | 53- 9.50% |

-continued

| Spike | 53- Cr(III) Spike | 54- Cr(VI) Spike |
|---|---|---|
| | 50- <0.00% | 50- >99.99% |
| | 52- <0.00% | 52- <0.00% |
| | 53- >99.99% | 53- <0.00% |

$$Crx(III) \frac{52}{53} \frac{83.79}{9.50} \qquad Crx(VI) \frac{52}{50} \frac{83.79}{4.35}$$

$$Crsp(III) \frac{52}{50} \frac{0.01}{99.99} \qquad Crsp(VI) \frac{52}{53} \frac{0.01}{99.99}$$

$$Crxsp(III) \frac{52}{53} \sim \frac{1}{1} \qquad Crxsp(VI) \frac{52}{50} \sim \frac{1}{1}$$

Where "x" is the sample specie, "sp" is the spike specie, and "xsp" is the final combination of sample and spike for a single specie.

The use of more than one speciated isotope provides the ability to calculate the contribution and conversion of one specie to another. This is very different from current methods wherein only the total in the final form can be determined and conversion is undesirable and unmeasurable.

If Example II were repeated but with isotopes of lesser purity, the same result could be achieved but the reduced purity of the isotopes would have to be considered in the calculations.

It will be appreciated that the present invention not only provides a basis for effective quantitative determination of the presence of a specie such as in a real, natural sample, but it facilitates use of the process in a batch or a continuous process as desired by the user. In addition, it provides a means for determining if there has been undesired conversion from one isotope or specie form to another during storage, as a result of interaction with reagent materials or during measurement. The process of spiking with one or more speciated isotopes of know concentration, quantity, and specie permits evaluation of various segments of specie analysis process. It also provides quality control measurement capability for evaluation of the validity of speciated procedures and standard methods. The ability to spike the sample at different stages provides evaluation beyond the ability to just measure the final specie concentration.

Spiked at a critical stage in a chemical procedure the conversion of various species with respect to that particular process can be evaluated and all subsequent procedures until mass ratio measurements are performed. Spiking during sampling provides a mechanism of evaluating the particular specie spiked from sample collection to final ratio measurement and provides a method of measuring the conversion for the entire protocol including storage, manipulation and the measurement process.

The ability to extract and separate the species from the bulk sample and material can be evaluated by spiking the sample and then extracting using such methods a microwave extraction, decomposition, solvent extraction. The conversion or interchange of the species with various procedures or for a single procedure can be measured. Correction for the process may be necessary to may procedures and this is the only method of providing a tracking procedure. This is crucial to the conversion from prescription based environmental and medical procedures to performance based methods. Performance based procedures require demonstration of the ability to achieve the precise speciated measurement required and precludes bias caused by conversion of other species.

It is desirable, where practical, to measure several species simultaneously on a qualitative and quantitative basis. To do this multiple isotope specie spikes are the most informative.

In order to employ the present invention in determining whether conversion has occurred, one should employ the double speciated isotopic spike such as is described in Example II.

Deconvolution of these species in the presence of each other may be determined using isotopic ratios such as, for example, CR(III) and CR(VI) species crossover by a species III to IV and vice versa shift will result in the isotope dement specie ratios being altered for each specie. Determination of the amount of crossover of one specie to another by using isotopic ratios to calculate the specie interchange becomes possible, employing the present invention.

Even where two isotopic spikes are not available, one spike can be used with calculation of crossover by ratio shift in one specie. An alternative is to perform the same speciated spiking experiment repeatedly but transform the isotopic spike into different species for different experiments. By collecting multiple measurements and doing a mass balance each time the entire speciation behavior mechanism can be evaluated.

It will be appreciated that the process is directed primarily toward elements, molecules, ions or complexes which have more than one isotope.

The invention may be employed in a wide range of applications including, but not limited to, medical, biological, environmental and industrial uses.

The invention enables measurement of elemental, ionic, and molecular species as well as complexes using isotope spiking of species, separation and isotope dilution fraction measurement to provide a combined technique enabling the reliable and definitive determination of the quantity of species in a real, natural sample.

The process of measurement may include the following features:

a. The preparation of species in elemental, ionic, molecular, organic metallic, complexed, and metallic states used in the speciated isotopic alteration of natural material containing natural species.

b. Equilibration of the species spike will be performed. In contrast to equilibration in classical IDMS, the elemental, ionic, molecular or complex species will be preserved. The isotopic spike will react in a manner similar to the natural isotopic species components. Equilibration in an aqueous sample will include mixing; in solid samples it may be extracted with the analyte of interest in the preparation methodology.

c. The physical and chemical separation of species containing isotopically altered species is performed to provide a time resolved component for each specie.

d. Extraction and physical separation may include, but not be limited to, extraction by microwave-assisted extraction, soxhilate extraction, solvent dissolution, acid dissolution, acid or base hydrolysis distillation, centrifugation, solvent extraction using a separatory funnel, and other chemical and physical separation methods.

e. Chromatographic separation may be used to separate the species in time and capture each fraction for separate evaluation by a mass spectrometer or in an on-line mode.

f. High performance liquid chromatography (HPLC) or flow injection analysis (FIA) may be used to separate the species is real time with detection of each fraction by a mass spectrometer.

g. Mass spectrometric measurements will be used to evaluate the isotopic element specie ratios of the specific specie fractions. This will produce an isotopic resolved component for evaluation. Isotope dilution calculations will be applied to each fraction to determine the quantitative concentration of the species present.

h. A shift in the isotopic ratios of other species not spiked with this specific isotope will be used to quantitatively determine the transformation of one species to another from the time of the spiking event. The original composition of the species composition will be calculated from these isotopic shifts.

i. Other algorithm calculations are possible from the two components of time resolution of individual species and mass isotopic element specie ratio alterations.

j. The method of the present invention makes it possible to measure the stability of species in specific reactions, separating reagents, chromatography procedures, extractions, at specific temperatures, and in various storage environments. Others are possible if spiked with speciated isotopes prior to the reaction occurring. Reactions affecting the natural material species will also affect the speciated isotopes. Ratio shifts in other natural species caused by the incorporation of the enriched isotopes into new molecular forms identifies the origin as the isotopically enriched specie.

k. These measurements may be made in active systems, such as environmental or biological systems, where spiking of the system with a specific species will be followed by isotopic shifts in species produced from the system. Examples may be the stable isotopic alteration of food and the evaluation of blood species components, urine, feces, and tissues using the equilibration of the natural system to perform the isotopic mixing and transformation of species. The same mathematical alterations may be used to deconvolve the final species. In addition, second spiking of another isotope of that same specie may be used to quantify the species, creating a double spike of different origin, one from the active biological or environmental system, and the other from the analytical process of measurement.

l. Stability of species may be determined by using isotope altered spikes of the species to track the stability and conversion with time, material, reagent, and other conditions.

The method of the present invention is applicable to elements, ions, inorganic molecules, complexes, covalent, organic molecules, organometallics, gasses, liquids, solids, solutions, and mixtures. Separated isotopic spikes of these same speciated forms can be created and thereby renders the method of the present invention a general technique to evaluate a variety of speciated forms in almost any sample matrix type. As stated hereinbefore, if desired, the process may be employed as a batch process or a continuous process.

Also, additional flexibility is provided in respect of what will be accomplished on-line as opposed to off-line. For example, on-line separation with off-line component evaluation may be employed. In the alternative, off-line sample preparation and spiking with on-line mass spectrometric analysis may also be employed, if desired. If desired, automatic spiking devices may add the speciated spike to the sample automatically or in a batch mode prior to analysis. Spiking of the sample may be achieved on-line with the isotopic spike being added in an automated fashion.

If desired, multiple isotopic spikes may be used simultaneously to evaluate species qualitatively or quantitatively. Isotopic spikes of the same specie but made from different isotopes can be added successively to the reaction to track reaction points where species alteration occurs at the greatest rate or to entirely different species. Different ratios will be produced in the related species depending on when the conversion occurred in the process.

It will be appreciated that the invention also contemplates spiking of the several different isotopically enriched analogs of the same specie which may be added at various steps in the sampling procedure and the stability and integrity of the specie with respect to these processes is evaluated by mass spectrometric measurements of the various isotopic ratios. Chemical processes, extraction methods, dissolution procedures and storage procedures may be evaluated.

Spiking active, biological and environmental systems with isotopic labelled species can be used to identify transformation of the species that permit fate and transport to be determined for species as well as providing the measurement method. The method may also be employed to evaluate the effect of precise energy inputs during extraction when employing energy inputting devices such as microwave energy controlled systems, super critical fluid extraction, or other solvent extraction systems to separate the species of interest from a matrix.

In connection with evaluation, the methods of the present invention may be employed, for example, in extraction chemistry, dissolution chemistry, chemical manipulation influences and storage chemistry.

The spiking of the sample in specific species separation devices such as microwave assisted chemical abstraction system permits the evaluation of the stability of the species extraction. Different temperatures and pressures conditions may shift the equilibrium of various species in the sample preparation of the sample. A previous patent application describes a method that permits the control of pressure at various temperatures in chemical reactions and in different phases in microwave chemical processing. See Kingston U.S. Ser. No. 08/127,263 filed on Sep. 24, 1993.

The spike of samples in specific species separation devices, such as chromatographic instrumentation, permits the evaluation of the stability of the species extraction and transforms the separation into a quantifiable technique. These devices may spike the sample automatically or in a batch mode. The speciated isotope dilution method may be used to evaluate the stability of the species extraction or to quantify the original species concentrations and method dependent devices.

The speciated enriched species may be added in a gas, liquid, solid or chemically or physically bound form.

It will be appreciated that a wide variety of mass spectrometric instruments can be used in the practice of the present invention. These include, but are not limited to, inductively coupled plasma mass spectrometry (ICP-MS), microwave induced plasma mass spectrometry (MIP-MS), thermal ionization mass spectrometry (TIMS), spark source mass spectrometry, liquid chromatography mass spectrometry (LC-MS), gas chromatography mass spectrometry (GC-MS), and all hyphenated and non-hyphenated mass spectrometric measurement techniques. Measurement by any mass discriminating device capable of isotopic measurement, including neutron activation analysis, can be used to make these measurements.

In the event that a suitable stable isotope were not available, a radiogenic isotope may be employed in lieu thereof and treated as a stable isotope for mass ratioing and such use shall be deemed to be a "stable isotope" for purposes of the disclosure and claims hereof.

The present method not only provides a capability not present in prior art techniques and one which is very much needed, but also one which can, depending upon instrument and method controls, provide the accuracy of highly accurate measurements.

In summary, the present invention provides an efficient means of obtaining accurate chemical specie quantitative evaluations in a manner which will have wide application and is not present in existing prior art systems.

Whereas particular embodiments of the invention have been described above for purpose of illustration, it will be evident that those skilled in the art that numerous variations of the details may be made without departing from the invention as defined in the appended claims.

I claim:

1. A method of isotope dilution measurement of a sample comprising:
    providing at least one predetermined, stable isotope,
    converting said stable isotope to a speciated enriched isotope corresponding to the species to be measured in said sample,
    spiking the sample containing said species to be measured,
    equilibrating said spiked species with said species to be measured, and
    separating all said species from said sample and subsequently determining the concentration of the species to be measured by employing isotopic element specie ratios.

2. The method of isotope dilution measurement of claim 1 including
    employing said method on more than one said species to be measured simultaneously.

3. The method of isotope dilution measurement of claim 1 including
    deconvoluting each species to be measured to determine if one such species to be measured has converted to another.

4. The method of isotope dilution method of claim 3 including
    employing a double speciated isotope spike in determining if isotope conversion has occurred.

5. The method of isotope dilution measurement of claim 1 including employing more than one said spike of said enriched isotope.

6. The method of isotope dilution measurement of claim 1 including
    employing a mass spectrometer to determine said isotopic element ratios.

7. The method of isotope dilution measurement of claim 6 including
tagging said enriched isotope with an isotopic tag in the same speciated form as the species to be measured.

8. The method of isotope dilution measurement of claim 6 including
determining the total concentration of both the specie of interest and the enriched isotope.

9. The method of isotope dilution of claim 1 including
employing time resolution chromatography to effect said separation.

10. The method of isotope dilution of claim 1 including
employing said method to determine the concentration of said species to be measured according to the formula:

Wherein:
$C_x$ is concentration of speciated element in the sample
$R_m$ is the measured isotope ratio of isotope A to isotope B
$A_x$ is atom fraction of isotope A in the sample (usually a constant ratio in nature)
$W_x$ is the weight of sample
$A_s$ is atom fraction of speciated isotope A in the spike (an enriched separated isotope)
$C_s$ is concentration of speciated elemental in the spike
$W_s$ is the weight of the isotopic spike
$B_x$ is atom fraction of isotope B in the sample (usually a constant ratio in nature)
$B_s$ is atom fraction of speciated isotope B in the spike (an enriched separated isotope).

11. The method of isotope dilution of claim 1 including
employing said method in determining the presence of at least one material selected from the group consisting of an elemental specie, an ionic specie, and a molecular specie.

12. The method of isotope dilution measurement of claim 1 including
adding said speciated enriched isotope to said sample on-line during said measuring process.

13. The method of isotopic dilution measurement of claim 1 including
effecting said conversion to said speciated enriched isotope online during said measuring process.

14. The method of isotope dilution measurement of claim 1 including
adding a plurality of said speciated enriched isotopes substantially simultaneously.

15. The method of isotope dilution measurement of claim 1 including
adding such speciated enriched isotope to a living biological system.

16. A method of isotope dilution processing of a sample comprising:
providing at least one predetermined, stable isotope,
converting said stable isotope to a speciated enriched isotope corresponding to the species to be measured in said sample,
spiking the sample containing said species to be measured,
equilibrating said spiked species with said species to be measured, and
separating all said species from said sample and subsequently determining the concentration of the species to be measured by employing isotopic element specie ratios, and
effecting said spiking at at least one of a predetermined time or predetermined event.

17. The method of isotope dilution processing of claim 16 including effecting said sampling at at least one specific time to measure process stability from such time to said concentration determination.

18. The method of isotope dilution processing of claim 16 including
employing said process for sampling during storage or separation.

19. The method of isotope dilution processing of claim 16 including
effecting said spiking with at least two said speciated enriched isotopes at different times to permit evaluation of stability of a specie of interest at different times.

* * * * *

UNITED STATES PATENT AND TRADEMARK OFFICE
CERTIFICATE OF CORRECTION

PATENT NO. : 5,414,259
DATED : May 9, 1995
INVENTOR(S) : HOWARD M. KINGSTON

It is certified that error appears in the above-identified patent and that said Letters Patent is hereby corrected as shown below:

In column 1, lines 30, 33, 56 and 64, "dement" should be --element--.

In column 6, line 58, "dement" should be --element--.

In column 9, line 1, "dement" should be --element--.

In column 13, line 24, "dement" should be --element--.

Signed and Sealed this

Second Day of April, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,414,259

DATED : May 9, 1995

INVENTOR(S) : HOWARD M. KINGSTON

It is certified that error appears in the above-identified patent and that said Letters Patent is hereby corrected as shown below:

Claim 10, column 17, line 17, after "formula:" the following equation should be inserted:

$$-- C_x = \frac{C_s W_s}{W_x} \cdot \frac{A_s - R_m B_s}{R_m B_x - A_x} --$$

Signed and Sealed this

First Day of May, 2001

Attest:

NICHOLAS P. GODICI

Attesting Officer            Acting Director of the United States Patent and Trademark Office